United States Patent
Banos et al.

(10) Patent No.: US 11,534,081 B2
(45) Date of Patent: Dec. 27, 2022

(54) METHODS OF AND DEVICES FOR MONITORING THE EFFECTS OF CELLULAR STRESS AND DAMAGE RESULTING FROM RADIATION EXPOSURE

(75) Inventors: Peter Theophilos Banos, Burlingame, CA (US); Robert Alfred Burmeister, Saratoga, CA (US)

(73) Assignee: Peter Theophilos Banos, Burlingame, CA (US)

( * ) Notice: Subject to any disclaimer, the term of this patent is extended or adjusted under 35 U.S.C. 154(b) by 1291 days.

(21) Appl. No.: 12/852,048

(22) Filed: Aug. 6, 2010

(65) Prior Publication Data

US 2011/0035158 A1    Feb. 10, 2011

Related U.S. Application Data

(60) Provisional application No. 61/273,521, filed on Aug. 6, 2009.

(51) Int. Cl.
| | |
|---|---|
| *A61B 5/08* | (2006.01) |
| *A61B 5/00* | (2006.01) |
| *G01N 33/497* | (2006.01) |
| *A61B 5/087* | (2006.01) |
| *A61B 5/091* | (2006.01) |

(Continued)

(52) U.S. Cl.
CPC .......... *A61B 5/082* (2013.01); *A61B 5/08* (2013.01); *A61B 5/087* (2013.01); *A61B 5/0836* (2013.01);

(Continued)

(58) Field of Classification Search
USPC .................................................. 600/532
See application file for complete search history.

(56) References Cited

U.S. PATENT DOCUMENTS

| | | |
|---|---|---|
| 4,012,145 A | 3/1977 | Chabannes et al. |
| 4,126,396 A | 11/1978 | Hartmann et al. |

(Continued)

FOREIGN PATENT DOCUMENTS

| | | | |
|---|---|---|---|
| WO | 0163277 A1 | 8/2001 | |
| WO | WO-2007082068 A2 * | 7/2007 | ......... A61K 38/2026 |

OTHER PUBLICATIONS

Dumitras et al., Investigation of human biomarkers in exhaled breath by laser photoacoustic spectroscopy, 2005, Proceedings of SPIE, vol. 5860, pp. 111-121.*

(Continued)

*Primary Examiner* — Michael R Bloch
(74) *Attorney, Agent, or Firm* — Haverstock & Owens, A Law Corporation

(57) ABSTRACT

Methods of and devices for detecting a measurable characteristic of the gas sample. The methods and devices are able to detect a value of or a change of measurable characteristic (e.g., such as chemical concentrations), a change of chemical compositions and/or biological responses of a living organism that are induced by a stressor. The biological responses are able to include cellular stress, damage, and immune responses. The stressor is able to include an exposure to ionizing radiation. The effects of the stressors are able to be monitored in terms of changes in the chemical concentrations and chemical compositions in an exhaled breath. The chemicals are able to function as bio-markers. The chemicals that are to be monitored are able to include nitric oxide, carbon monoxide, carbon dioxide, ethane, and other molecules related to specific disease resulting from the stressor.

6 Claims, 3 Drawing Sheets

(51) Int. Cl.
*A61B 5/083* (2006.01)
*A61N 5/10* (2006.01)

(52) U.S. Cl.
CPC .............. *A61B 5/091* (2013.01); *A61B 5/417* (2013.01); *A61B 5/4848* (2013.01); *G01N 33/497* (2013.01); *A61N 5/1031* (2013.01)

(56) References Cited

U.S. PATENT DOCUMENTS

| | | | | |
|---|---|---|---|---|
| 5,447,165 | A | * | 9/1995 | Gustafsson .......... A61B 5/0813 600/532 |
| 5,538,494 | A | * | 7/1996 | Matsuda .......................... 600/1 |
| 5,645,072 | A | * | 7/1997 | Thrall et al. .................. 600/532 |
| 5,848,975 | A | | 12/1998 | Phillips |
| 5,922,610 | A | * | 7/1999 | Alving ............... G01N 33/0037 422/83 |
| 6,010,459 | A | * | 1/2000 | Silkoff ................... A61B 5/097 128/200.26 |
| 6,038,913 | A | * | 3/2000 | Gustafsson .......... A61B 5/0813 600/531 |
| 6,076,005 | A | * | 6/2000 | Sontag et al. ................ 600/413 |
| 6,099,480 | A | | 8/2000 | Gustafsson |
| 6,544,190 | B1 | * | 4/2003 | Smits ................... A61B 5/0836 600/529 |
| 6,594,016 | B1 | | 7/2003 | Te Lintel Hekkert et al. |
| 6,733,463 | B2 | | 5/2004 | Moilanen et al. |
| 7,427,269 | B2 | * | 9/2008 | George .................. A61B 5/083 600/529 |
| 2002/0026937 | A1 | * | 3/2002 | Mault .................. A61B 5/0002 128/200.24 |
| 2003/0109795 | A1 | * | 6/2003 | Webber ................ A61B 5/0836 600/543 |
| 2003/0208133 | A1 | * | 11/2003 | Mault .................. A61B 5/0002 600/532 |
| 2005/0010110 | A1 | * | 1/2005 | Black et al. .................. 600/436 |
| 2005/0085877 | A1 | * | 4/2005 | Kratz ............................. 607/94 |
| 2005/0245835 | A1 | | 11/2005 | Butler et al. |
| 2006/0017009 | A1 | * | 1/2006 | Rink ........................ G01T 1/161 250/484.5 |
| 2006/0034726 | A1 | * | 2/2006 | Sunshine et al. ............... 422/58 |
| 2006/0253176 | A1 | * | 11/2006 | Caruso ................. A61B 18/203 607/88 |
| 2007/0167694 | A1 | * | 7/2007 | Causevic ............. A61B 5/0402 600/301 |
| 2008/0033412 | A1 | * | 2/2008 | Whelan .................... A61N 5/01 606/11 |
| 2008/0283062 | A1 | * | 11/2008 | Esposito, Jr. .......... A61B 5/061 128/204.23 |
| 2009/0124918 | A1 | | 5/2009 | Stockmann et al. |
| 2009/0309046 | A1 | * | 12/2009 | Balakin ...................... 250/492.3 |
| 2010/0035869 | A1 | * | 2/2010 | Wipf .................... A61K 31/454 514/227.2 |

OTHER PUBLICATIONS

Harren et al., On-line laser photoacoustic detection of ethene in exhaled air as biomarker of ultraviolet radiation damage of the human skin, 1999, Applied Physics Letters, vol. 74, No. 12, pp. 1761-1763.*

A.R. Wewel et al., "Time Course of Exhaled Hydrogen Peroxide and Nitric Oxide During Chemotherapy", European Respiratory Journal, 2006; pp. 1033-1039, vol. 27 No. 5, DOI: 10.1183/09031936. 06.00101705, GroBhansdorf, Germany.

Koizumi et al., "Influence of Thoracic Radiotherapy on Exhaled Nitric Oxide Levels in Patients with Lung Cancer." Jpn. J. Clin. Oncol. (2001) 31 (4):142-146.

Arterbery et al., "Breath ethane generation during clinical total body irradiation as a marker of oxygen-free-radical-mediated lipid peroxidation: A case study." Free Radical Biology and Medicine, vol. 17, Issue 6, Dec. 1994, pp. 569-576.

Hamid et al., "Induction of nitric oxide synthase in asthma," Lancet, vol. 342, Dec. 18-25, 1993, pp. 1510-1513.

Kharitonov et al., "Increased nitric oxide in exhaled air of asthmatic patents." Lancet, Jan. 1994, vol. 343, pp. 133-135.

Persson et al., "Single-breath nitric oxide measurements in asthmatic patients and smokers." Lancet, 1994, vol. 343, pp. 146-147.

Ryter, S.W. and Otterbein, L.E., "Carbon monoxide in biology and medicine." BioEssays, 2004, vol. 26, Issue 3, pp. 270-280.

Nakagawa et al., "Dose- and Time-Dependence of Radiation-Induced Nitric Oxide Formation in Mice as Quantified with Electron Paramagnetic Resonance." Nitric Oxide: Biology and chemistry, 2001, vol. 5, No. 1., pp. 47-52.

Shao et al., "Nitric Oxide-Mediated Signaling in the Bystander Response of Individually Targeted Glioma Cells." Cancer Research, vol. 63, Issue 23, Dec. 1, 2001, pp. 8437-8442.

Nozaki et al., "Nitric oxide as an inflammatory mediator of radiation pneumonitis in rats." American Journal of Physiology—Lung Cellular and Molecular Physiology, vol. 272, Issue 4, 1997, pp. L651-L658.

Wang, C. and Sahay, P., "Breath Analysis Using Laser Spectroscopic Techniques: Breath Biomarkers, Spectral Fingerprints, and Detection Limits." Sensors, Oct. 19, 2009, vol. 9, pp. 8230-8262.

Shorter et al., "Multicomponent Breath Analysis With Infrared Absorption Using Room-Temperature Quantum Cascade Lasers." IEEE Sensors Journal, vol. 10, No. 1, Jan. 2010, pp. 76-84.

Namjou et al., "The Breathmeter: A New Laser Device to Analyze Your Health." IEEE Circuits and Devices Magazine, Sep./Oct. 2006, pp. 22-28.

Crohns et al., "Exhaled pentane as a possible marker for survival and lipid peroxidation during radiotherapy for lunch cancer—a pilot study." Free Radical Research, Oct. 2009, vol. 43, No. 10, pp. 965-974.

Phillips, Dr. Michael, "Rapid, Non-Invasive Radiation Bio-Dosimeter." Abstract. Nov. 7, 2005, Menssana Research, Inc., Fort Lee, New Jersey 07024.

Kwa et al., "Radiation pneumonitis as a funciton of mean lung dose: an analysis of pooled data of 540 patients." Int J. Radiat. Oncol. Biol. Phys., Aug. 1, 1998, 42(1) pp. 1-9.

Alving et al., "Increased amount of nitric oxide in exhaled air of asthmatics." European Respiratory Journal, 1993, vol. 6, pp. 1368-1370.

* cited by examiner

METHODS OF AND DEVICES FOR MONITORING THE EFFECTS OF CELLULAR STRESS AND DAMAGE RESULTING FROM RADIATION EXPOSURE

CROSS-REFERENCE TO RELATED APPLICATION

This patent application claims priority under 35 U.S.C. 119 (e) of the U.S. Provisional Patent Application Ser. No. 61/273,521, filed Aug. 6, 2009, and titled "A monitor for the effects of radiation exposure," which is hereby incorporated by reference for all purposes.

FIELD OF THE INVENTION

The present invention relates to the field of bio-sensing. More specifically, the present invention relates to the field of chemical sensing after a radiation exposure to a biological substance.

BACKGROUND OF THE INVENTION

Radiation therapy is a modality employed against a large variety of tumors, but it is limited by the effects of radiation on the patient, as well as on the tumor. Some patients suffer significant side effects, including radiation pneumonitis, bone marrow suppression, and other effects. Others are able to benefit from higher doses than the doses actually used, but the higher doses are withheld for fear of causing unacceptable side effects. Susceptibility to radiation induced pathology varies from person to person, and likely from time to time. While appropriate radiation dosing is a matter of careful planning, any individual's personal susceptibility or resistance to radiation damage at any given time can only be guessed before radiation therapy. After radiation therapy when symptoms of radiation induced injury begin to develop, an individual's personal susceptibility to radiation induced damage is able to be better assessed. Nonetheless, it is already too late to hold or withdraw the radiation dose that has already been given.

Approximately one million patients undergo radiation therapy each year in the United States. Patients undergo multiple fractionated radiation sessions. Many of those sessions are able to have the potential to cause side effects, including radiation pneumonitis, anemia, radiation burns, thyroiditis, and more. There is therefore a clinical need to minimize each radiation dose, as well as the cumulative radiation dose. At the same time, each of the radiation sessions has the purpose of causing regression to the tumor or tumors for which the patients are being radiated. The need to cause as much tumor regression as possible translates into a clinical need to maximize each radiation dose, as well as the cumulative radiation dose. The need to minimize the radiation doses is obviously in conflict with the need to maximize the radiation doses. The appropriate balance must be struck, but it varies from patient to patient, and from time to time for each patient. Individual optimization for each patient and for each radiation session is therefore a challenge.

At the present time, the ex-ante parameters for individualization of each radiation session are only minimally quantifiable. One radiation effect which might be better managed by such individualization is radiation pneumonitis. Radiation pneumonitis has been studied as a function of mean lung dose in statistically significant pools of patients, but there is, as yet, no way to optimally monitor (as opposed to model) the toxicity of any given dose of radiation for any given patient.

Radiation pneumonitis has been found to affect approximately 10% of patients undergoing radiation therapy for lung cancer. At the same time, the tumor regression of lung cancer after radiation therapy is minimal. Those patients who develop radiation pneumonitis likely cause radiation oncologists to minimize radiation doses to all patients undergoing thoracic radiation, which is consistent with the principle of primum non nocere. Among the patients who do not develop radiation pneumonitis are likely those who could have withstood far higher doses of radiation, which would be more likely to cause significant tumor regression. Identifying the radiation sensitive group and the radiation resistant group is able to allow a reduction in radiation side effects for the sensitive group and perhaps greater tumor regression for the resistant group. Accordingly, better methods and devices that are able to measure and determine a required or an optimal radiation dosage are needed.

SUMMARY OF THE INVENTION

To better determine the required or optimal radiation dosage, a detection apparatus is used to monitor and/or detect the concentration of one or more substances in exhaled breath. The detection is able to be performed before, upon, during, and/or after the exposure of the radiation. A person skilled in the art would appreciate that "radiation" is used as an example. Any other stressors that are able to cause biological or physiological responses are applicable, such as applied lighting, temperature, smells, or any other conditions that are able to affect a human's physiological condition like chemical agents, toxins, infectious organisms, and chemotherapy. The detection apparatus provides frequent and/or continuous measurements of the substances in exhaled breath. These measurements are able to be used to create a database of these measurements versus clinical events. These clinical events are able to include radiation dose, tumor regression, radiation pneumonitis, or others. When the database is established, the detection apparatus is able to be used to allow comparison of measurements with database values, which enables or aids prognoses of future clinical events. This comparison also allows alteration of stressors, such as radiation therapy, guided by the biomarker measurements in exhaled breath and in conjunction with the database described.

In first aspect, a method of detecting a measurable characteristic of the gas sample comprises receiving a gas sample containing a targeting chemical generated by a testee and determining a measurable characteristic of the gas sample before, during or after, or some combination of before, during, or after a stressor event to the testee by using an analytic device. In some embodiments, the stressor event comprises exposure to radiation. In other embodiments, the radiation comprises a medical ionizing radiation. In some other embodiments, the gas sample comprises an exhaled breath. In some embodiments, the testee comprises an animal. In other embodiments, the animal comprises a human. In some other embodiments, the targeting chemical comprises nitric oxide. In some embodiments, the targeting chemical comprises carbon dioxide. In other embodiments, the targeting chemical comprises carbon monoxide. In some other embodiments, the targeting chemical comprises nitrous oxide. In some embodiments, the method further comprises correlating the change with the stressor event, such that an effect of the stressor event is able to be determined. In other embodiments, the method further comprises initiating or optimizing a therapy to the testee, wherein the therapy does not use the stressor event. In some other embodiments, the method further comprises adjusting the stressor event to optimize a therapy to the testee, wherein the therapy uses the stressor event. In some embodiments, adjusting the stressor event comprises adjusting a dosage of the stressor event. In other embodiments, the optimization of the therapy comprises improving a prognosis, outcome, or a combination thereof of the therapy. In some other embodiments, the optimization of the therapy comprises altering a dosage in real time while applying the stressor event. In some embodiments, the measurable characteristic comprises a quantity. In other embodiments, the quantity comprises a mass, an amount, or a concentration of the targeting chemical in the gas sample. In some other embodiments, the quantity comprises a flow rate or a volume of the gas sample. In some embodiments, determining the quantity is performed before the stressor event. In other embodiments, determining the quantity is performed after the stressor event. In some other embodiments, determining the quantity is performed during the stressor event. In some embodiments, the method further comprises determining a change of the quantity caused by the stressor event. In other embodiments, determining the quantity is performed before and during the stressor event and determining the change of the quantity is performed during or after the stressor event. In some other embodiments, determining the quantity is performed before and after the stressor event and determining the change of the quantity is performed after the stressor event. In some other embodiments, determining the quantity is performed during and after the stressor event and determining the change of the quantity is performed after the stressor event. In some embodiments, the stressor event comprises exposure to a chemical agent, a toxin, or any combination thereof. In other embodiments, the stressor event comprises exposure to an infectious organism. In some other embodiments, the stressor event comprises exposure to a chemotherapy. In some embodiments, the targeting chemical comprises acetone, acetaldehyde, ammonia, butane, carbon monoxide, carbon disulphide, carbon dioxide, carbonyl sulfide, ethane, ethanol, ethylene, hydrogen, an H/D isotope, hydrogen peroxide, hydrogen cyanide, 8-isoprostane, isoprene, methane, methanethiol, methanol, methylated amines, methyl nitrate, nitrogen monoxide, nitrotyrosine, oxygen, pentane, pyridine, sulfur compounds, or hydrocarbons. In other embodiments, the hydrocarbons comprise toulene, benzene, decane, styrene, octane, or pentamethylheptane. In some other embodiments, the method further comprises taking the breath sample for contemporaneous or non-contemporaneous analysis one or more times before a stressor event, one or more times during a stressor event, or one or more times after a stressor event.

In second aspect, a method of determining an effect caused by exposure to radiation comprises obtaining one or more gas samples from one or more exhaled breaths of an animal, determining one or more quantities of one or more chemicals contained in the breath or breaths of the animal, allowing the animal to be exposed to a stressor, wherein the stressor comprises radiation, again determining one or more quantities of one or more chemicals contained in the breath or breaths of the animal, and determining a change in the quantity of the measured chemical or chemicals across the multiple determinations. In some embodiments, the animal comprises a human. In other embodiments, the chemical comprises a bio-marker. In some other embodiments, the chemical comprises a volatile organic compound. In some embodiments, the chemical comprises carbon monoxide, carbon dioxide, nitric oxide, nitrous oxide, or a combination thereof. In other embodiments, the change is used to adjust the dosage of the radiation. In some other embodiments, the quantity or quantities of one or more compounds are determined before exposure to radiation, during to radiation, after exposure to radiation, or any combination thereof. In some embodiments, the first concentration, the second concentration, or both is determined by using infrared spectroscopy.

In third aspect, a system for measuring a biological response to a radiation exposure comprises a sensing member capable of detecting a measurable characteristic of a gas sample generated by a biological substance, a gas collector fluidly coupling with the sensing member, such that the gas sample collected is able to be transferred to the sensing member, and a software system in a computing device coupling with the sensing member, wherein the software is capable of determining the measurable characteristic of the gas sample.

In some embodiments, the software is capable of determining a change of the measurable characteristic caused by a radiation event. In other embodiments, the measurable characteristic comprises a mass, an amount, or a concentration of a targeting chemical in the gas sample. In some other embodiments, the measurable characteristic comprises a flow rate, a volume of the gas sample, or both. In some embodiments, the system further comprises a laser-based spectroscopic system. In other embodiments, the system further comprises a database in the computing device. In some other embodiments, the database comprises earlier data, which is able to be used for comparison of later data or data from a current measurement. In some embodiments, the comparison is able to show an effect of the radiation, such that a dosage of the radiation is able to be adjusted based on the comparison. In other embodiments, the sensing member comprises infrared spectroscopy other than laser-based spectroscopy, mass spectroscopy, gas chromatography, liquid chromatography, high-performance liquid chromatography, raman spectroscopy, or a combination thereof. In some other embodiments, the software system is able to predict the biological response.

DETAILED DESCRIPTION OF THE PREFERRED EMBODIMENT

Figure 1:
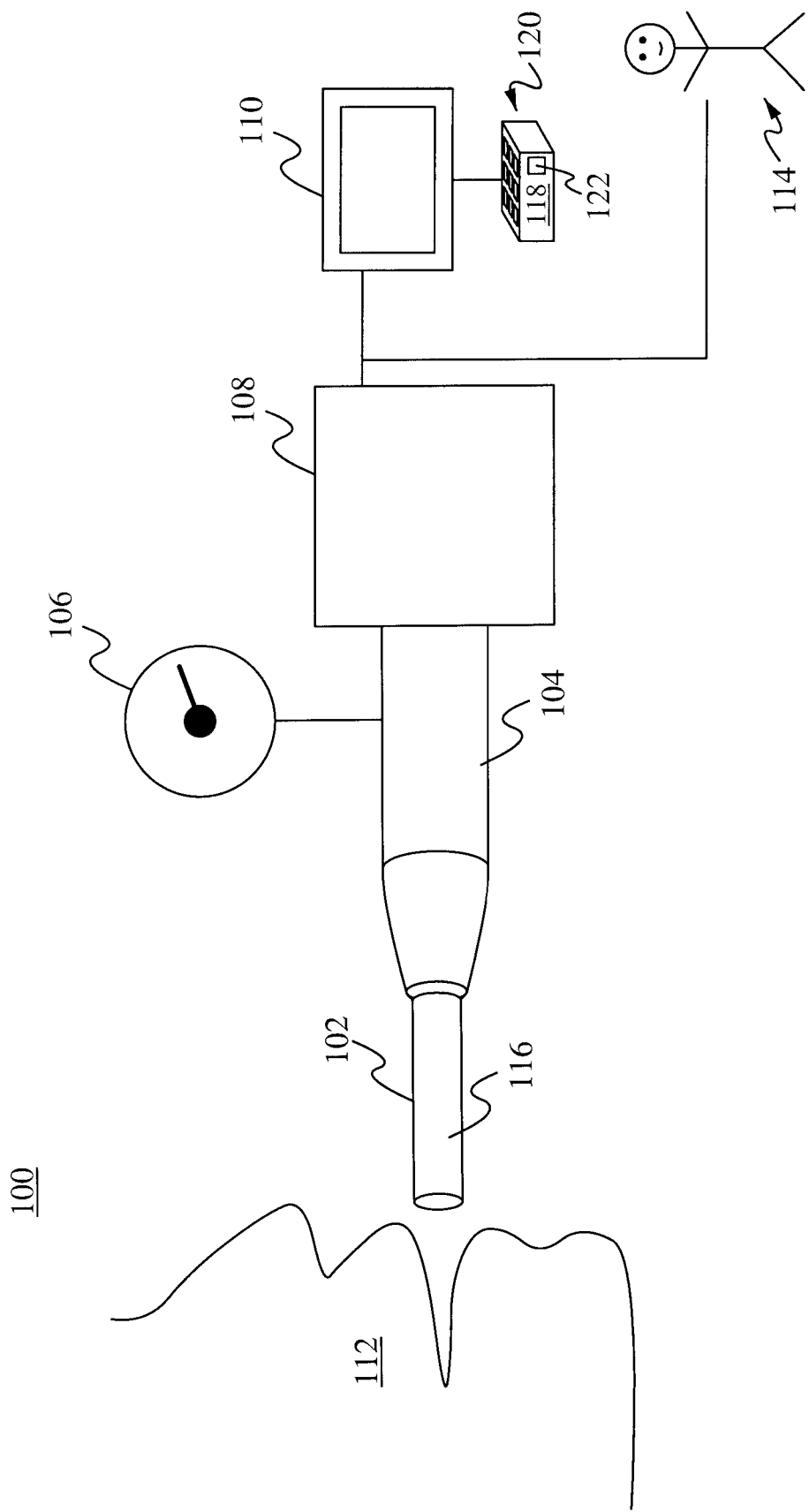
FIG. 1 illustrates a device for chemical content and concentration analysis and monitoring of an exhaled breath in accordance with some embodiments.

Embodiments of the present application are directed to the methods of and devices for chemical analysis of an exhaled breath. Those of ordinary skill in the art will realize that the following detailed description of the methods of and devices for chemical analysis of an exhaled breath are illustrative only and are not intended to be in any way limiting. Other embodiments of the methods of and devices for chemical analysis of an exhaled breath will readily suggest themselves to such skilled persons having the benefit of this disclosure.

Reference will now be made in detail to implementations of the methods of and devices for chemical analysis of an exhaled breath as illustrated in the accompanying drawings. The same reference indicators will be used throughout the drawings and the following detailed description to refer to the same or like parts. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In some embodiments, methods of and devices for analyzing exhaled breath to monitor the effects of ionizing radiation exposure are provided. The component of the exhaled breath is capable of reflecting the volatile chemicals of the tissues and fluids through the exhaled breath that passes on the way out of the body. The breath component is therefore able to be used as markers for the biochemical milieu of the body from which the exhaled breath is sampled.

The methods and devices disclosed herein are able to show that the contents and concentrations of exhaled breath are able to vary upon exposure to ionizing radiation. The contents of exhaled breath are able to contain nitric oxide, nitrous oxide, carbon dioxide, and carbon monoxide. The changes of the contents and concentrations of the chemicals in the exhaled breath are able to be measured. Further, the methods and devices disclosed herein are able to show that variation of the exhaled breath content with exposure to ionizing radiation are able to vary from individual-to-individual, vary with radiation doses, and is able to be correlated to clinical events such as the development of radiation pneumonitis.

The changes of the concentration and/or content of the chemicals in the exhaled breath are able to be associated with the symptoms resulting from the exposure of the stressor. The chemicals include some volatile chemicals, such as nitric oxide and carbon monoxide, which are known or suspected to be associated with parameters related to cellular metabolisms, with inflammation, or with both. For example, nitric oxide (NO), is known to be linked to airway inflammation and to smoking Airway inflammation is at least one of the underlying pathologies that is associated with radiation pneumonitis and it's sequela. In another example, carbon monoxide is known to be associated with cytoprotection during inflammation. Cytoprotection during inflammation is able to occur in living cells subsequent to ionizing radiation exposure.

Methods of and devices for measuring above-mentioned chemicals in the exhaled breath are disclosed. In some embodiments, ARI Breath Analyzer, Aerodyne Systems, Billerica, Mass. are used in conjunction with the methods and devices disclosed for the measurements. The measurements include analyzing the chemical changes that result from exposure to ionizing radiation.

In the following, the methods of and devices for measuring the chemical contents and concentration and their changes in the exhaled breath before, upon, during, and/or after the stressors are disclosed in accordance with some embodiments. FIG. 1 illustrates a device 100 for chemical content and concentration analysis and monitoring of an exhaled breath in accordance with some embodiments. In some embodiments, the device 100 comprises a collection apparatus 102, connecting hoses 104, a sensor 106, a detector 108 and a monitor 110. A person skilled in the art would appreciate that the above-mentioned components are examples, and all components described above are optional. Any additional components are able to be added when proper.

The collection apparatus 102 is able to collect exhaled breath from a testee 112. The collection apparatus 102 is able to include a face mask, such as face mask 202 (FIG. 2A), or a tube member 116 capable of being held in the mouth of the testee 112. The connecting hose 104 is able to transport samples of exhaled breath to the sensor 106 and/or the detector 108. The sensor 106 is able to be a mass sensor, a volume meter, or any other measuring device that is able to be used in or near the collection apparatus 102, the connecting hoses 104, and/or the detector 108 to measure the mass or volume of exhaled breaths. A person skilled in the art would appreciate that the sensor 106 is able to be any quantitative and analytical device capable of measuring the volume, weight, density, flow rate, odor, breath frequency, the strength of the exhaled breaths, and any other physical, chemical, biological, physiological property of the testee 112. Further, a person skilled in the art would appreciate that the testee 112 is able to be human, domestic animal, wild animal, a dish of bacteria, or any other biological or non-biological substances that are able to generate gases or detectable chemicals.

The detector 108 is able to analyze the exhaled breath and allow frequent measurement of substances, including exhaled gasses, in the exhaled breath. The detector 108 is able to contain a laser spectrometer, or other devices of sufficient sensitivity, specificity, and other attributes to allow adequate quantification of selected exhaled substances to allow analysis. In some embodiments, the detector 108 is able to include various analytical and separation devices, such as gas chromatography (GC), liquid chromatography (LC), and high-performance liquid chromatography (HPLC) with and/or without asymmetrical separation columns.

In some embodiments, the output of the detector 108 and associated measuring devices such as the sensor 106 are able to be combined to provide measurements of concentration of selected exhaled substances or measurement of total mass of exhaled substances. The measurements of concentration, mass, or both of exhaled substances are able to be provided to the monitor 110 to be further processed or to be observed by a person 114, such as a physician, a medical related person, or a technician.

In some embodiments, the monitor 110 comprises a data processing unit 118. The data processing unit 118 is able to compile and calculate measurement data received from the detector 108 and sensor 106 and information stored in a storage device 122, such as a hard disk or memory. The data that is processed by the data processing unit 118 and/or stored in the storage device 122 is able to form a database 120. In some embodiments, the database 120 is able to contain a measurement date of concentration and mass of exhaled substances. In some other embodiments, the database 120 is able to contain the measurement date combining with data of other clinical events. In some embodiments, the clinical events include radiation dose, tumor regression, radiation pneumonitis, or others. The database 120 with elements of the above-mentioned measurements of concentration or exhaled substances, mass of exhaled substances, and clinical events, is able to be established and grow with the accumulation of data.

The information in the database 120 including stored database values, such as measurements of concentration and/or mass of exhaled substances, is able to be compared with subsequent measurements. As such, the database 120 is able to enable and/or aid the prognosis of future clinical events. The comparison of data is also able to be used for the alteration of radiation therapy or the alteration of side effect treatment/prophylaxis guided by the measurements in exhaled breath. In some embodiments, the alteration of radiation therapy is able to be performed in real time allowing optimization of radiation dosing to be sought.

Figure 2A:
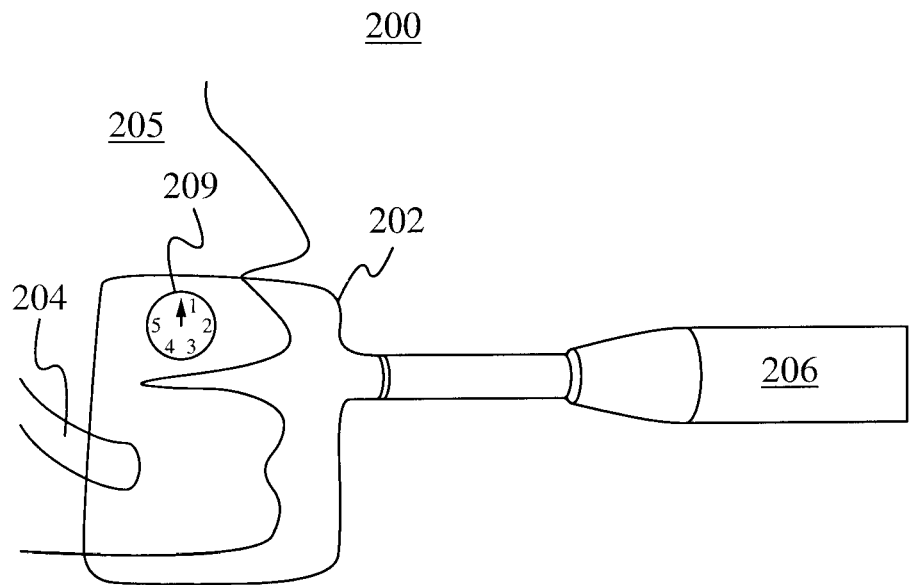
FIGS. 2A and 2B illustrate a collection apparatus in accordance with some embodiments.
Figure 2B:
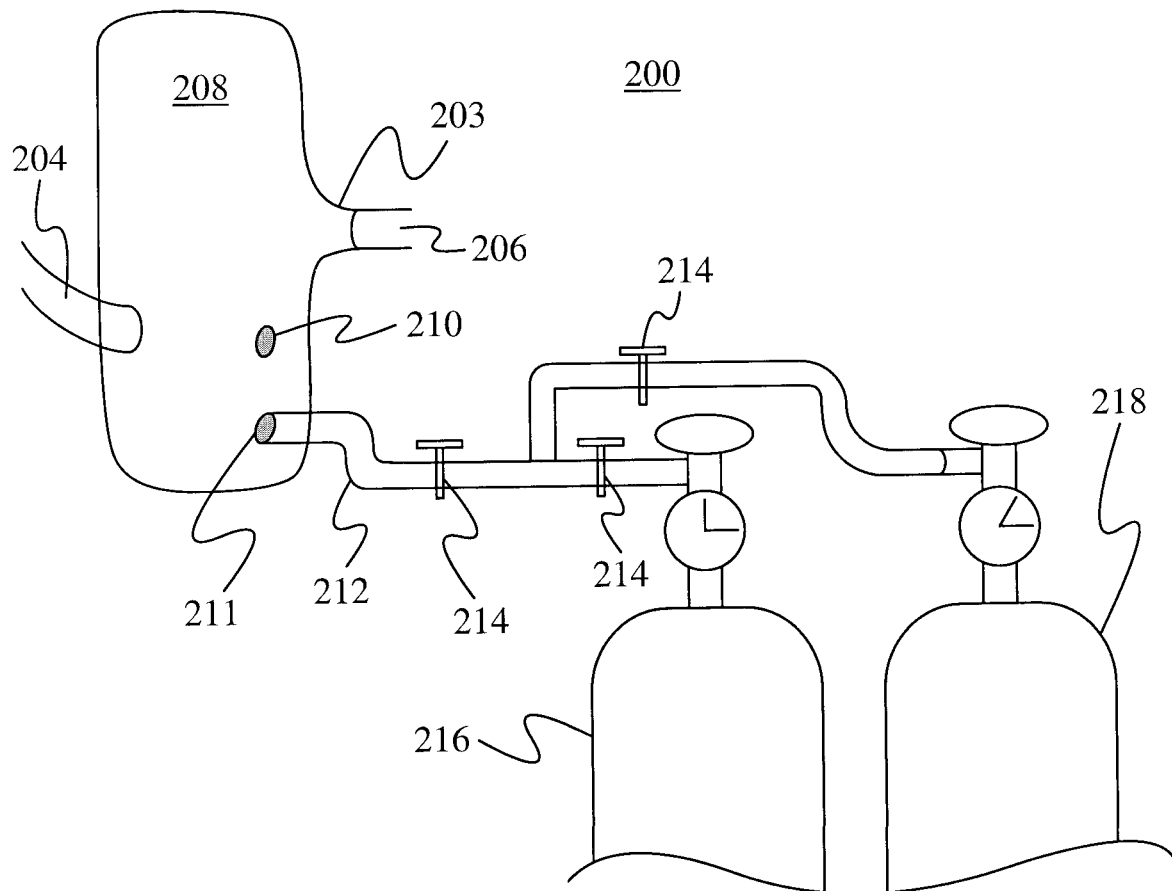

In the following, some designs of the collection apparatus 102 (FIG. 1) are described. FIGS. 2A and 2B illustrate a collection apparatus 200 in accordance with some embodiments. The collection apparatus 200 are able to include face masks 202 and 208. In some embodiments, the face masks 202 and 208 comprise one or more straps 204, a connecting port 203, or a combination thereof. The strap 204 is able to contain an elastic plastic or a rubber band capable of retaining the face mask on the testee 205. The connecting port 203 is able to be coupled with a connecting hose 206, which is able to be coupled with the sensor 106 (FIG. 1) and the detector 108 (FIG. 1), so that a sample generated by the testee 205 is able to be received by the device 100 (FIG. 1). In some embodiments, the face mask 208 comprises an air valve 210 allowing single or directional flow of air. In some other embodiments, the face mask 208 comprises a gas port 211. The gas port is able to be coupled with hose 212 and valves 214, which are able to be coupled with supplemental gas tanks 216 and 218. The supplemental gas tank is able to contain any gases desired. For example, the gas tank 216 is able to contain oxygen, which is able to be supplied for the comfort of and a need for oxygen supplementation for the testee 205. In another example, the gas tank 218 is able to contain compressed air or nitrogen gas, such that a diluted sample is able to be provided. A person skilled in the art would appreciate that any gases are able to be used so long as the gas is able to facilitate the sample analysis.

In some embodiments, the collection apparatus 200 comprises a simple hose, into which the patient breathes intermittently. This provides an easy way to measure the exhaled gasses and is able to allow measurements of multiple concentrations with each exhalation. Multiple measured concentrations during the exhalation process are able to be matched to different portions of the respiratory anatomy. In some other embodiments, the collection apparatus 200 comprises a valved face mask 208 to fit over the nose and mouth. The valve 210 is able to allow air into the mask from the room or from a source of purified air, such as the gas tank 218. In some other embodiments, the valved face mask 208 comprises a mask that is easy to wear and easy to breathe through. In some embodiments, the valved face mask 208 introduces some dead space, represented by the volume between the mask inner surface and the surface of the face. The dead space is able to be minimized or reduced by custom-fitting a mask for each patient. The custom-fitting is able to be done with standard machining or plastic molding or with three dimensional printing tools. In some embodiments, the collection apparatus 200 comprises a modified non-rebreather face mask 202 provided with sensitive flow meters 209 and a measured supply of incoming filtered air. The measured mass and volume of gas, entering and exiting the mask, are able to be combined with the measured concentration of compounds of interest exiting the mask to derive the concentration of compounds of interest in the exhaled breath. In some embodiments, the collection apparatus 200 comprises a sampling tube that is held near, but not in, the mouth allowing measurement of compounds of interest in the stream of exhaled breath as the breath exits the mouth.

Figure 3:
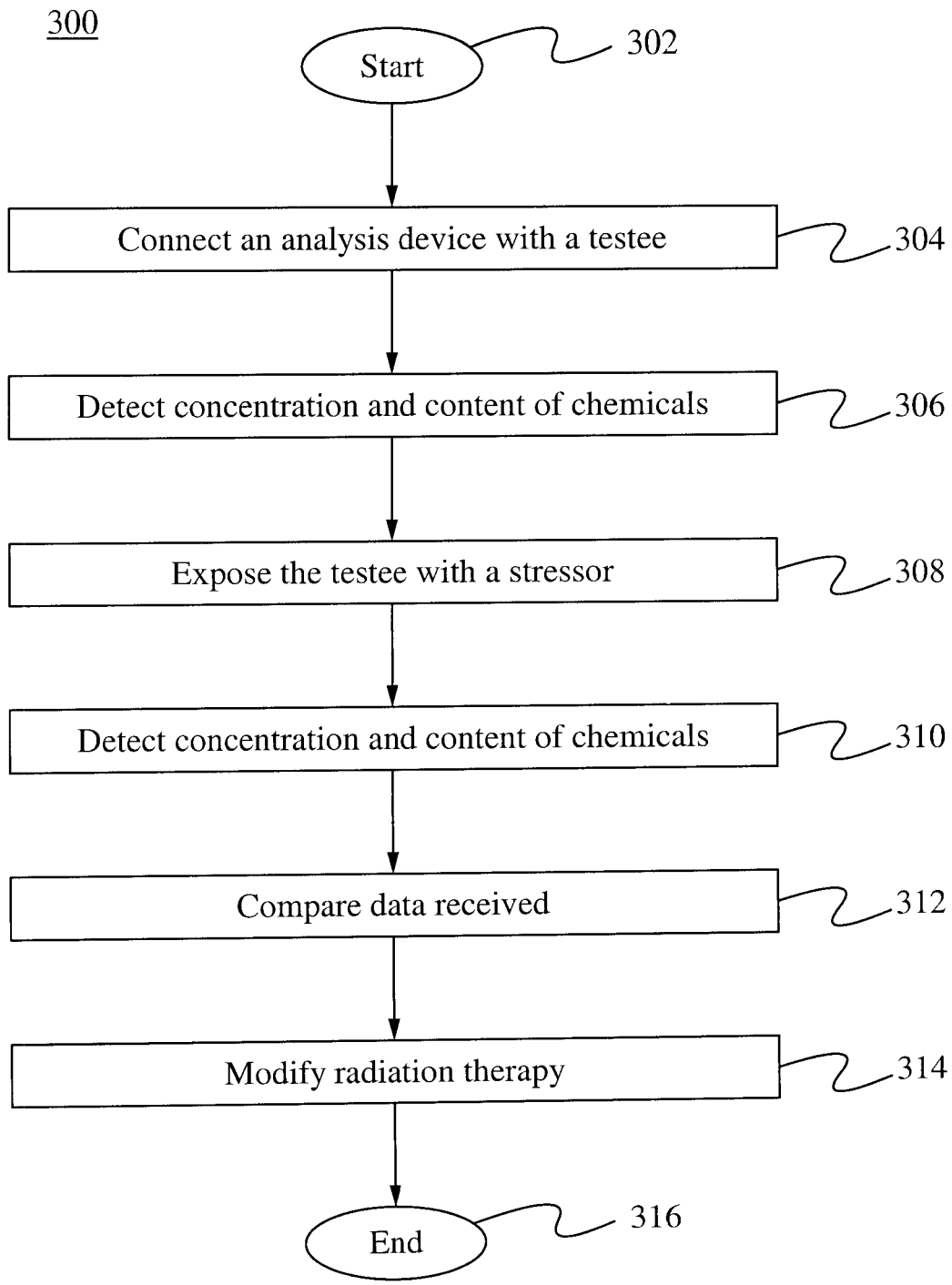
FIG. 3 is a flow chart illustrating a method of monitoring the chemical concentration and content changes caused by the application of stressors in accordance with some embodiments.

In the following, methods of monitoring the effects of stressors on a testee are provided. FIG. 3 is a flow chart illustrating a method 300 of monitoring the chemical concentration and content changes caused by the application of stressors in accordance with some embodiments. The method 300 is able to begin from Step 302. At Step 304, an analytic device is coupled with a testee. The analytic device is able to be the device 100 (FIG. 1) for chemical content and concentration analysis and monitor of an exhaled breath. At Step 306, concentrations and contents of chemicals are detected by using the analytic device. The contents of the chemicals are able to include types of molecules, specific functional groups (such as alcohol groups), specific elements (such as sulfur), biological substances, and any other chemicals that are able to be generated by the testee. The concentrations of the chemicals are able to be in the level of ppm (parts-per-million), ppb (parts-per-billion), ppt (parts-per-trillion), or any other concentration levels up to the detection limit of the analytical device. At Step 308, the testee is exposed to a stressor. The stressor is able to be any radiations, ionized particles, energy waves, sound waves, or any other energy forms so long as the physiological condition of the testee is able to respond to the stressor and generate detectable changes to the monitored chemicals or transformation of the chemicals. For example, a molecule with an aldehyde group is able to be transformed into an acid group. Accordingly, the transformation of the chemicals induced by the application of the stressor is able to include REDOX reactions, electron transfer reactions, and any other chemical and/or biological reactions. At Step 310, the changes to the concentrations and contents of the chemicals are able to be detected, and the data of the changes are collected and stored. At Step 312, the data collected after the exposure of the stressor is compared with the data collected before the exposure of the stressor. At Step 314, the comparisons of the data are used to assist the adjustment of the therapy, such as adjusting the dosage used for a radiation treatment. The method 300 ends at Step 316. A person skilled in the art would appreciate that the method described above is an implementation in accordance with some embodiments, and the steps described above are all optional. Additional and extra steps are able to be added when proper.

First Selected Exemplary Experiment:

In the following, exemplary experiments based on the method 300 described above are performed. An analytic device, such as the device 100 (FIG. 1), is used to measure the changes of nitric oxide in the exhaled breath. Nitric oxide is associated with inflammation and is known, in animals, to be associated with radiation exposure. In some examples, the analytic device comprises a laser measuring device for gas analysis, which is able to measure nitric oxide at concentrations down to hundreds of parts per trillion. The changes of the level/concentration of the exhaled nitric oxide are monitored/measured before, upon, during, and after radiation exposure. In some other experiments, testees with thoracic tumors are selected for the experiments. Testees with thoracic tumors are expected to have radiation exposure to the respiratory organs, mainly the lungs (the lungs and associated structures being the single common organs though which exhaled compounds of interest all have to pass before being measured as exhaled substances.) In some other experiments, testees with lung cancer are selected for the experiments. Lung cancer almost invariably includes the lungs. The rates of radiation pneumonitis after radiation therapy are particularly high and regression/cure rates after radiation therapies are particularly low.

The experimental designs of some of the above exemplary experiments are discussed in the following. In some of the exemplary experiments, nitric oxide levels are measured in the expired air from patients with lung cancer undergoing radiation therapy. Each measured nitric oxide level is time-stamped, so that each nitric oxide level with the events of radiation therapy is able to be correlated, including the amount of radiation exposure. The gas samples are able to be collected and analyzed in such a way that measurements of differential nitric oxide levels from different portions of the respiratory tree are able to be done.

In the following, results of some of the exemplary experiments based on the method 300 described above are discussed. The changes in the concentration of nitric oxide levels in exhaled breath are able to be identified. The levels of nitric oxide concentrations at any given time are able to be described, and thus the first and second derivatives of the nitric oxide levels are able to be obtained in exhaled breath. Discontinuities in the data are sought, which includes points at which a higher-order derivative of the concentration of nitric oxide changes from zero to a nonzero value.

In some other exemplary experiments, measurement of differential nitric oxide levels from different portions of the respiratory tree (as opposed to measuring the average nitric oxide levels from each breath) are performed and analyzed. For such exemplary experiments, modifications of the laser measuring device's sampling equipment are able to be performed, which allow sampling many times during each breath. In some embodiments, the actual time required for a nitric oxide level measurement in a given gas sample is on the order of fractions of second, so measuring multiple compound concentrations during each breath is therefore a matter of presenting samples to the laser measuring device quickly. The data processing part of some of the exemplary experiments includes correlating changes in the measured concentrations of compounds of interest with other parameters relating to radiation dosing and to the effects of that radiation dosing.

Second Selected Exemplary Experiment:

In the following exemplary experiments, a detection apparatus is used to monitor the concentration of one or more substances in exhaled breath before, upon, during and/or after exposure to stressors, such as a dose of radiation. The detection apparatus is able to provide frequent or continuous measurements of the substances in exhaled breath. The measurements are able to be used to create a database of these measurements versus clinical events. These clinical events are able to include radiation dose, tumor regression, radiation pneumonitis, or others.

In some of the exemplary experiments, the detection apparatus includes laser-based breath detector provided by Aerodyne Research, Billerica Mass. The Aerodyne breath detector accepts a gas sample, such as an exhaled breath. A mid-infrared laser beam is split into two paths and one is passed through the gaseous sample and the second serves as a reference beam. The wavelength of the laser source is scanned over the spectrum including the absorption peaks or bands of the molecules of interest. The two beams impinge upon a photodetector sensitive in the region of interest, and the ratio of the two beams results in an electrical signal characteristic of the contents of the gas sample being evaluated. That electrical signal, or measurements reflecting the electrical signal, is then able to be used to determine the characteristics of the gas sample being evaluated. A database of such spectral data is able to be established, and the detection apparatus is used to allow comparison of measurements with database values. As such, the devices and methods disclosed herein enable diagnosis and aid in the prognosis of future clinical events. The comparison also allows alteration of stressors, such as radiation therapy, guided by the bio-marker measurements in exhaled breath, likely in conjunction with the database described.

In some of the exemplary experiments, near instantaneous measurements of breath components are able to be obtained. The speed of the measurement that is able to be obtained includes at least two significant effects. First, the short sensing time for each measurement allows multiple measurements to be made during each breath. This is a significant difference between photonic methods of breath analysis and a method such as that based on sol-gel technology. Because different parts of each breath stream originate in different parts of the respiratory tree, those multiple measurements made during each breath allow differentiation of breath components that originate in different parts of the respiratory tree. Thus, data from breath that comes from the nose, for example, is able to be differentiated from data that comes from the alveoli. This is able to be particularly relevant in a case in which a significant stress (such as radiation exposure) is visited upon the alveoli, while the nose is relatively free of such stress. Second, the short sensing time required for each measurement of breath analysis allows more rapid, verging on real time, actions to be taken in response to the changes monitored by the breath analysis system. This is able to allow, for example, alteration of radiation dosing quickly. In a case in which analysis indicates advisability of a reduction in dosing, such a reduction is able to be done as soon as possible, rather than continuing radiation dosing while a slower analysis system is still collecting a sample and generating data.

Third Selected Exemplary Experiment:

In the following exemplary experiments, a patient is scheduled for a radiation therapy. Before the exposure of a dose of radiation, a preliminary sample of breath would be taken to be analyzed at that time or at a later time. Such analysis is able to include a detection of concentrations of nitric oxide, carbon monoxide, carbon dioxide, and nitrous oxide. Radiation therapy is able to be delivered to the patient in a manner consistent with the prescription of a radiation oncologist. Such radiation therapy is able to have 2 Gy of ionizing radiation 5 days a week for 6 weeks. At various points during and after the therapy, other breath samples are able to be taken for contemporaneous or non-contemporaneous analysis. The points at which such breath samples are taken, is able to be after every radiation dose or a fraction of the radiation dose. Alternatively, the points that the breath samples are taken are able to be after the delivery of all the radiation doses. Analysis of those breath samples, and the changes thereof, is able to be performed. The analysis is able to be delivered to the radiation oncologist.

In some of the exemplary experiments, the data provided is able to be used in multiple ways to improve medical management. For example, alteration of radiation dosing is able to be performed. As discussed above, some of the exemplary experiments allow such alteration of radiation dosing to be performed in, or near, real time. Persons who are found to have biochemical responses to radiation exposure (as measured by the devices and methods disclosed herein) consistent with a particularly high sensitivity to radiation are able to have their radiation dose lowered. The lowering of the dose is able to be performed in real time. On the other hand, persons who are found to have biochemical responses to radiation exposure consistent with a particularly low sensitivity to radiation are able to have their radiation dose raised. The increasing of the dose is able to be performed in real time. Further, the treatment for radiation side effects is able to be improved. Much of the treatment for radiation side effects, such as radiation pneumonitis, awaits development of symptoms by the patient. Use of the above-mentioned methods and devices to identify persons who are more likely, for example, to develop such pneumonitis or who are in a pre-symptomatic phase of such pneumonitis, are able to allow earlier initiation of therapeutic measures, such as, for example, steroid administration.

A person skilled in the art would appreciate that the above listed chemicals or the bio-markers to be detected are examples of some of the embodiments, and any other bio-markers are able to be selected for the detection so long as the chemicals/bio-markers are detectable by the devices and/or methods disclosed herein. For example, the bio-markers are able to include, but not limited to, acetone, acetaldehyde, ammonia, butane, carbon monoxide, carbon disulphide, carbon dioxide, carbonyl sulfide, ethane, ethanol, ethylene, hydrogen, H/D isotope, hydrogen peroxide, hydrogen cyanide, 8-isoprostane, isoprene, methane, methanethiol, methanol, methylated amines, methyl nitrate, nitrogen monoxide, nitrotyrosine, oxygen, pentane, pyridine, sulfur compounds, and hydrocarbons (such as toulene, benzene, decane, styrene, octane, and pentamethylheptane.) Further, the laser system is able to include, not limited to, infrared lasers (such as tunable infrared laser differential absorption spectroscopy (TIDAS)), quantum cascade (QC) lasers, and lead-salt diode lasers. The infrared lasers are able to include mid-IR, far-IR, near IR, or any other IR wavelength regions. Furthermore, the sensors are able to include mass spectroscopy (MS), selected ion flow tube mass spectroscopy (SIFT MS), proton transfer reaction (PTR) MS, and any other spectroscopy or measuring devices, such as devices for measuring weight, volume, and flow rate.

A person skilled in the art will appreciate that the exhaled breath tests/chemical concentration analysis is able to be taken at any time. For example, one or more exhaled breath tests/analysis are able to be taken before the testee receives any radiation treatments. The test results, obtained before the testee receives any radiation treatments, are able to be used to optimize treatment plans. In some other examples, one or more exhaled breath tests/analysis are able to be taken after the testee receives at least some amount of radiation treatment. In some other examples, one or more exhaled breath tests/analysis are able to be taken before the testee receives radiation treatments and one or more exhaled breath tests are able to be taken after the testee receives at least a portion of a dosage, a full dosage, or multiple dosages of radiation treatment. In some examples, all of the concentration measurements are able to be performed before the stressor event. In other examples, all of the concentration measurements are able to be performed during the stressor event. In some other examples, all of the concentration measurements are able to be performed after the stressor event. "Concentration" is one of the examples of a characteristic that is able to be measured in accordance with the embodiments. Other measurable characteristics including and not limited to a mass, an amount, or a concentration of the targeting chemical in the gas sample and flow rate or volume of the gas sample is able to be measured.

The methods and devices described herein are able to be utilized to monitor and/or detect the concentrations of one or more substances in exhaled breath, such that changes of the concentrations and contents of the chemicals (e.g., biomarkers) in exhaled breath are able to be detected and/or monitored.

In operation, the devices disclosed herein are coupled with a testee and measurements are taken before, upon, during, and/or after the exposure of the stressor. The methods and devices provided herein provide advantageous aspects including assisting the adjustment of the dosage of the stressor (e.g., radiation), such that the stressor amount/dosage are able to be optimized for individual patients.

All the steps that are contained in the methods/procedures described above are some embodiments of the present application. All the steps are optional and all the steps when applicable are able to be performed in any sequences or order as desired. Additional steps are also able to be added when a person skilled in the art deem proper.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A system for measuring a biological response to a radiation exposure comprising:
   a) a stressor generator generating ionizing radiation for application to a biological substance, the ionizing radiation comprising a dosage level;
   b) a nitric oxide sensing member configured to measure concentrations of nitric oxide:
      in at least one first exhaled breath stream by the biological substance before application of the ionizing radiation to the biological substance,
      in at least one second exhaled breath stream during application of the ionizing radiation to the biological substance, and
      in at least one third exhaled breath stream after application of the ionizing radiation to the biological substance;
   c) a gas collector with a sampling tube fluidly coupled to the nitric oxide sensing member and configured to collect and transfer one or more of the at least one first exhaled breath stream, the at least one second exhaled breath stream and the at least one third exhaled breath stream to the nitric oxide sensing member; and
   d) a computing device coupled to the nitric oxide sensing member, wherein the computing device is configured to control the generating of the ionizing radiation dosage level or an adjustment in a concentration of the dosage level of the ionizing radiation generated by the stressor generator, by comparing a change in nitric oxide concentration in one or more selected modes, wherein the selected modes comprise:
      i) comparing change of nitric oxide concentration in the second exhaled breath stream exhaled during application of the ionizing radiation to the first exhaled breath stream exhaled before application of the ionizing radiation;
      ii) comparing change of nitric oxide concentration in the third exhaled breath stream exhaled after application of the ionizing radiation to the second exhaled breath stream exhaled during application of the ionizing radiation;

iii) comparing change of nitric oxide concentration in the third exhaled breath stream exhaled after application of the ionizing radiation to the first exhaled breath stream exhaled before application of the ionizing radiation; and iv. comparing change of nitric oxide concentration in one or more of:

the at least one first exhaled breath stream exhaled before application of the ionizing radiation, the at least one second exhaled breath stream exhaled during application of the ionizing radiation, and the at least one third exhaled breath stream exhaled after application of the ionizing radiation, to one or more values of stored exhaled nitric oxide concentration measured data.

2. The system of claim 1, wherein the nitric oxide sensing member is further configured to measure a characteristic including a flow rate, a volume of gas sample, or both.

3. The system of claim 1, wherein the nitric oxide sensing member further comprises a photonic-based spectroscopic system.

4. The system of claim 1 further comprising a database configured to store the one or more values of stored exhaled nitric oxide concentration measured data which includes earlier data used for comparison of later data, or configured to store data from a current measurement.

5. The system of claim 1, wherein the nitric oxide sensing member comprises spectroscopy other than laser-based spectroscopy, mass spectroscopy, gas chromatography, liquid chromatography, high-performance liquid chromatography, raman spectroscopy, or a combination thereof.

6. The system of claim 1, wherein the nitric oxide sensing member is further configured to measure a concentration of carbon monoxide.

* * * * *